United States Patent [19]
Kotler

[11] Patent Number: 5,615,689
[45] Date of Patent: Apr. 1, 1997

[54] METHOD OF PREDICTING BODY CELL MASS USING BIOIMPEDANCE ANALYSIS

[75] Inventor: Donald P. Kotler, New Rochelle, N.Y.

[73] Assignee: St. Luke's-Roosevelt Hospital, New York, N.Y.

[21] Appl. No.: 353,933

[22] Filed: Dec. 12, 1994

[51] Int. Cl.$^6$ .................................................. A61B 5/05
[52] U.S. Cl. .................................................. 128/734
[58] Field of Search .................................. 128/734, 774, 128/630, 632, 693, 741

[56] References Cited

U.S. PATENT DOCUMENTS

| | | | |
|---|---|---|---|
| 4,911,175 | 3/1990 | Shizgal | 128/734 |
| 4,947,862 | 8/1990 | Kelly | 128/734 |
| 5,086,781 | 2/1992 | Bookspan | 128/734 |
| 5,335,667 | 8/1994 | Cha | 128/734 |
| 5,449,000 | 9/1995 | Libke et al. | 128/734 |

OTHER PUBLICATIONS

Henry C. Lukaski, "Methods for the assessment of human body composition: traditional and new," 46 Am. J. Clin. Nutr. 537 (1987).
Robert F. Kushner, "Bioelectrical Impedance Analysis: A Review of Principles and Applications," 11 J. Am. Coll. Nutr. 199 (1992).
Henry C. Lukaski et al., "Validation of tetrapolar bioelectrical impedance method to assess human body composition," 60 J. Appl. Physiol. 1327 (1986).
Robert F. Kushner et al., "Estimation of total body water by bioelectrical impedance analysis," 44 Am. J. Clin. Nutr. 417 (1986).
David McDougall et al., "Body Composition Measurements from Whole Body Resistance and Reactance," 37 Surg. Forum 42 (1986).
Henry C. Lukaski et al., "Assessment of fat-free mass using bioelectrical impedance measurements of the human body," 41 Am. J. Clin. Nutr. 810 (1985).
Ronald E. Young et al., "Bioelectrical-impedance analysis as a measure of body composition in a West Indian population," 55 Am. J. Clin. Nutr. 1045 (1992).
Elizabeth A. Conlisk et al., "Predicting body composition from anthropometry and bioimpedance in marginally undernourished adolescents and young adults," 55 Am. J. Clin. Nutr. 1051 (1992).
Annemie MWJ Schols et al., "Body composition by bioelectrical-impedance analysis compared with deuterim dilution and skinfold anthropometry in patients with chronic obstructive pulmonary disease," 53 Am. J. Clin. Nutr. 421 (1991).
Karen R. Segal et al., "Estimation of extracellular and total body water by multiple-frequency bioelectrical-impedance measurement," 54 Am. J. Clin. Nutr. 26 (1991).
Herman L. Johnson et al., "Predicting Total Body Water and Extracellular Fluid Volumes from Bioelectrical Measurements of the Human Body," 11 J. Am. Coll. Nutr. 539 (1992).

T. E. M. S. Sluys et al., "Body Composition in Patients with Acquired Immunodeficiency Syndrome: A Validation Study of Bioelectric Impedance Analysis," 17 JPEN 404 (1993).
Centers for Disease Control, "Classification System for Human T–Lymphotropic Virus Type III/Lymphadenopathy–Associated Virus Infections," 105 Ann. Intern. Med. 234 (1986).
Richard N. Pierson, Jr., et al., "Total–body potassium in health: effects of age, sex, height, and fat," 226 Am. J. Physiol. 206 (1974).
Donald P. Kotler et al., "Body composition studies in patients with the acquired immunodeficiency syndrome," 42 Am. J. Clin. Nutr. 1255 (1985).
Richard N. Pierson, Jr., et al., "Body potassium by four–pi $^{40}$K counting: an anthropometric correction," 246 Am. J. Physiol. F234 (1984).
R. N. Pierson, Jr., et al., "Body Composition Measurements in Normal Man: The Potassium, Sodium, Sulfate and Tritium Spaces in 58 Adults," 35 J. Chron. Dis. 419 (1982).
Francis D. Moore et al., "Body Cell Mass and Limits of Hydration of the Fat–Free Body: Their Relation to Estimated Skeletal Weight," 110 Ann. N.Y. Acad. Sci. 62 (1963), reprinted in 4 Nutr. 277 (1988).
M. Barac–Nieto et al., "Body composition in chronic undernutrition," 31 Am. J. Clin. Nutr. 23 (1978).

(List continued on next page.)

*Primary Examiner*—Max Hindenburg
*Attorney, Agent, or Firm*—Brumbaugh, Graves, Donohue & Raymond

[57] ABSTRACT

The inability to precisely estimate body composition using simple, inexpensive and easily applied techniques is an impediment to clinical investigations in nutrition. In this study, predictive equations for body cell mass (BCM), fat free mass (FFM), and total body water (TBW), were derived, using single frequency bioimpedance analysis (BIA), in 332 subjects, including white, black and hispanic men and women, both normal healthy controls and patients infected with the human immunodeficiency virus (HIV). Preliminary studies demonstrated more accurate predictions of BCM when using parallel transformed values of reactance than the values reported by the bioimpedance analyzer. Modeling equations derived after logarithmic transformation of height, reactance and impedance were more accurate predictors than equations using height$^2$/resistance, and the use of gender-specific equations further impoved accuracy. The addition of weight to the modeling equation also improved accuracy but was less important than the impedance measurements. The resulting equations were internally validated, and race, disease (HIV infection) and malnutrition were shown not to affect the predictions. The equation for FFM also was validated externally against results derived from hydrodensitometry measurements in a group of 440 healthy individuals, with a standard error of the estimate of under 5%. These results indicate that body composition can be estimated accurately using simple, inexpensive, and easily applied techniques, and that the estimates are sufficiently precise for use in clinical investigation and clinical practice.

4 Claims, No Drawings

OTHER PUBLICATIONS

H. M. James et al., "Whole body cellular and collagen nitrogen in healthy and wasted man,:" 67 Clin. Sci. 73 (1984).

G. Babameto et al., "Alterations in Hydration in HIV–Infected Individuals," 42 Clin. Reas. 279A (Abstract, 1994).

Ellen Engelson et al., "Effects of Megestrol Acetate Therapy upon Body Composition and Serum Testosterone in AIDS," 42 Clin. Reas. 281 A (Abstract, 1994).

Paul Deurenberg et al., "Changes in fat–free mass during weight loss measured by bioelectrical impedance and by densitometry," 49 Am. J. Clin. Nutr. 33 (1989).

Jorge A. Vazquez et al., "Validity of bioelectrical–impedance analysis in measuring changes in lean body mass during weight reduction," 54 Am. J. Clin. Nutr. 970 (1991).

Gilbert B. Forbes et al., "Is bioimpedance a good predictor of body–composition change?," 56 Am. J. Clin. Nutr. 4 (1992).

METHOD OF PREDICTING BODY CELL MASS USING BIOIMPEDANCE ANALYSIS

Recent developments in the field of body composition analysis have increased the accuracy of estimation of the different body compartments in normal individuals (1–3). However, the ability to assess body composition in the clinical arena has lagged behind scientific and technological developments. Research techniques such as whole body counting, isotope dilution, dual photon absorptiometry, total body electrical conductivity, in vivo neutron activation analysis, and others have limited availability, are expensive to develop and maintain, and are technologically difficult to perform, thus limiting their applicability in field studies.

Bioimpedance analysis (BIA) has shown great potential in its ability to estimate body composition. The method is based upon assuming the body to be a cylindrical-shaped ionic conductor, with the extracellular and intracellular, non-adipose tissue compartments acting as resistors and capacitors, respectively (4). Initial studies indicated that total body water (TBW) volume was more closely related to height$^2$/resistance than to height/resistance, as predicted from the theoretical model (5,6). Those studies also showed that reactance (capacitance) did not add to the accuracy of predicting TBW (5,6). Many investigators have developed empiric equations for predicting TBW, extracellular and intracellular water volumes, lean body mass, body cell mass, and body fat content utilizing weight, age, gender, race, or other variables in addition to height and resistance (7–16). However, the body is not shaped as a simple cylinder. In addition, the lack of effect of reactance in predicting TBW does not negate its potential use in predicting other body composition parameters. Furthermore, few studies have compared the predictability of BIA as a function of race, gender or disease.

The purpose of this study was to derive predictive equations for the estimation of body cell mass (BCM), fat free mass (FFM), and TBW using single frequency BIA. Studies were performed in a large, diverse group of study subjects, including white, black and hispanic men and women, and in healthy subjects as well as subjects infected with the human immunodeficiency virus. Predictive equations were derived from direct measurements; BCM by determination of total body potassium (TBK), FFM and fat content by dual X ray absorptiometry, and TBW by $^2$H$_2$O dilution. The usefulness of using reactance in the predictive models for BCM, FFM, and TBW was determined. The precise relationship between height and the impedance values, resistance and reactance, was evaluated using an exponential approach to regression analysis. The resulting predictive models were internally validated and their relative accuracy in men and women, whites, blacks and hispanics, and in healthy people versus those infected with the human immunodeficiency virus (HIV) were determined. In addition, the predictive model derived from the current data set for FFM was compared to calculations based upon studies performed in a large group of healthy controls, in whom fat free mass was determined by hydrodensitometry.

METHODS

Subjects

This was a retrospective, cross-sectional analysis of studies performed in the Body Composition Unit at St. Luke's-Roosevelt Hospital Center. The studies had been approved by the Institutional Review Board and subjects signed informed consent for the procedures. Three hundred thirty two subjects were studied, including 206 men and 126 women, of whom 134 were HIV-infected and 198 were normal controls (Table 1). HIV infection was confirmed by ELISA testing with Western blot confirmation, or fit the standard case definition for AIDS (17). Studies of HIV serostatus had not been performed in the control group. The mean age of the study group was 40 years, and were similar in HIV-infected and control subgroups.

Measurements

Total body potassium content, an estimate of body cell mass was measured in a 4 pi whole body liquid scintillation counter, as described previously (18,19). The attenuating effect of body fat was corrected for using $^{42}$K calibration (20). The precision of this technique is 2.6% on calibration standards and 4% on human subjects. Body fat content was determined by dual photon absorptiometry (Lunar Corp) using software provided by the manufacturer (21). The precision of the measurement is 1.8%. Fat free mass was calculated from weight and body fat content. Total body water was taken as the volume of distribution of $^3$H$_2$O with correction for hydrogen exchange, as described previously (22). The precision of the method is 2.8%.

Single frequency BIA was performed at 50 kH and 800 uA (RJL 101A, RJL Systems) using standard tetrapolar lead placement (5). Both resistance (R) and reactance (Xc) were determined. The reproducibility of the measurement on repeated measurements in the laboratory was 1.1%. Body weight was determined to the nearest 0.1 kg using a calibrated beam balance and standing height was measured to the nearest 2 mm.

Development of predictive models using BIA

Predictive models for BCM, FFM, and (TBW) were developed in a standardized fashion. In preliminary studies using the whole data set, the use of the resistance and reactance values reported by the BIA analyzer and their parallel transformed values were compared. The resistance and reactance values calculated and reported by the BIA instrument are based upon measuring a series electrical circuit containing a resistor and capacitor (Rudy J. Liedtke, personal communication). However, the actual reactance of a capacitor differs when placed in a series or parallel electrical circuit. As shown in FIG. 1, the extracellular water (resistor) and non-adipose tissue cells (capacitors) are arranged as a parallel electrical circuit (23). Conversion of resistance and reactance to their parallel values was accomplished using standard equations (24), as described below.

The role of the reactance measurement in predicting body composition was reevaluated. Most investigators have ignored this measurement and have used only the measured resistance in their calculations. The predictability of the measured and parallel transformed values of resistance and reactance were compared. In addition, the use of the calculated impedance (Z) in predicting body composition was determined. Impedance is defined by the equation, $Z^2=R^2+Xc^2$.

Preliminary studies also examined the relationships between height and R, Xc, or Z. The theoretical model for bioimpedance assumes that the body is roughly shaped as a cylinder whose volume can be estimated as height$^2$/R (3,5). Previous studies showed that height$^2$/R predicted TBW more accurately that did the use of height/R (5,6). However, the relationships between height, R and Xc likely are more complex, since the body is not shaped exactly like a cylinder, or even a group of cylinders representing the trunk, arms and legs (4). For example, men tend to have broader chests, narrower hips and more muscular upper arms and thighs than women. Predictive models for BCM, FFM, and TBW were developed using a multiple regression technique, after logarithmic conversion of R, Xc, Z, and height. The use of log transformed values allows for analysis of exponential relationships to be assessed directly. Such interactions are not possible using standard regression analyses. The relationships between height and R, Xc or Z were compared in men and women. The predictability of the resulting exponential equations were compared to equations derived using $height^2/R$. The effect of adding weight to the predictive equation then was determined.

The preliminary studies indicated that the use of parallel transformed values of Xc may improve the accuracy of the predictive equations, that $height^2/R$ is not the most accurate reflection of all body compartments, that the precise relationship may differ in men and women, and that the inclusion of weight increases the accuracy of prediction (see below). Subsequent validation studies were performed based upon these preliminary results.

Validation of the predictive equations

The procedure for validation of the different body composition parameters also was standardized. Initially, the whole study group was divided randomly into two subgroups, a model group and a validation group. A predictive equation was derived in the model subgroup, and regression parameters were compared in the model and validation subgroups. If the regression coefficients and standard errors of the estimates, as well as the means and standard deviations of the predicted and actual measurements were not different, statistically, the derived model was taken as valid for the the overall study group. The predictive model derived from the whole study group was used in further studies.

The effects of race and disease (HIV infection) were evaluated separately. The effect of race was evaluated by comparing regression parameters in gender-specific equations applied to people of different races. In a similar manner, comparisons were made in HIV-infected and non-infected subjects. RESULTS Body composition in HIV-infected and control groups The body composition results are shown in Table 2. The measured values of weight, BCM (as TBK), BCM normalized by height, and FFM were lower in control women than in control men, while body fat content was higher in women than in men. The HIV+ subgroups had lower values for weight, BCM, TBW, fat and FFM than did race and gender-matched controls. As opposed to gender, race had a less important influence upon body composition. Of note, differences in BCM or FFM accounted for a majority of the weight differences between HIV+ and control males, while differences in fat mass accounted for the majority of the differences in weight between HIV+ and control women.

Preliminary validation studies

As stated above, the resistance and reactance values reported by BIA are based upon a series electrical circuit containing a resistor and capacitor, while the extracellular water (resistor) and body cell mass (capacitor) can be seen as a parallel electrical circuit. Parallel reactance can be calculated from the series or measured reactance using the equation: $Xc_p = Xc_M + R_M^2/Xc_M$, with $Xc_M$=measured reactance, $R_m$= measured resistance, and $Xc_p$= parallel transformed reactance. In the same manner, parallel resistance is calculated as: $R_p = R_M + Xc_M^2/R_M$ (24). Series and parallel impedance are equal. The predictability of using the measured (series) or the parallel transformed BIA measurements were compared by simple regression analysis using the complete data set (Table 3). BCM was most accurately predicted using $Xc_p$ while FFM and TBW were more accurately predicted using Z or R. The correlation coefficient between BCM (TBK) and $height^2/Xc_m$ was 0.28 with a standard error of the estimate of 22.8%. In contrast, the correlation coefficient between BCM and $height^2/Xc_p$ was 0.85, with a standard error of 12.7% (Table 3). Thus, $Xc_p$ was used as the BIA value for estimating BCM, while Z was chosen as the BIA value to estimate FFM and TBW.

Predictive models for BCM, FFM and TBW then were developed using the whole data set and a multiple regression technique, after logarithmic conversion of $Xc_p$ or Z, and height. The use of log transformed values allows for interactions between variables, especially exponential relationships, to be assessed directly. The regression equation can be stated as $Y=\exp[k_1 LOG(Xc \text{ or } Z)+k_2 LOG(height)+k_3]$. The results were compared to regressions performed using $Ht^2/Xc$ or Z. As shown in Table 4, the use of exponential relationships increased the correlation coefficients for both BCM and FFM, with minimal effects on the prediction of TBW. Furthermore, derivation of separate equations for men and women substantially increased the correlation coefficients and decreased the standard errors of estimate for BCM and FFM, again with minimal effects on TBW. Thus, modeling after logarithmic transformation of the $Xc_p$ or Z may be more representative of the body's complex shape than the use of $height^2/Xc_p$ or Z.

The effect of adding body weight to the gender-specific equations then was evaluated (Table 5). Addition of body weight further improved their accuracy (r=0.96, SEE=5.45% for FFM, r=0.91, SEE=9.96% for BCM, r=0.91, SEE= 7.78% for TBW (FIG. 2). Validation studies were performed using these equations.

Validation of the predictive models for BCM, FFM, TBW

The study group was divided into model and validation subgroups, and predictive equations were derived in the model group. The correlation coefficients and standard errors of the estimate between measured and predicted values of BCM, FFM and TBW were similar in the two subgroups (Table 6). Thus, the proposed model, using capacitance, resistance and height appears to be valid for the range of subjects evaluated in this study.

The effects of race, HIV infection and malnutrition upon the accuracy of predicting fat free mass were determined using the gender-specific equations, as described in methods. Neither race or HIV infection affected the accuracy of the predictive model (Table 7).

The validity of the predictive equation for FFM was evaluated further by comparing the results of BIA to estimates of FFM obtained using hydrodensitometry in a group of 440 college age men and women studied previously (data on file at RJL Systems). Calculations of FFM by BIA averaged about 3.3 kg lower than did estimates made by densitometry (FIG. 3). However, the correlation coefficient between the BIA and hydrodensitometry estimates was 0.98, and the standard error of the BIA estimate was 4.99% of the mean. Thus, the predictive equations for BIA from our laboratory are valid when used to analyze data obtained in another laboratory using the same type of BIA analyzer.

The accuracy of predicting BCM, FFM and TBW by BIA was compared to predictions using weight alone or body mass index (wt/ht$^2$)(Table 8). The correlation coefficients were much lower when using weight or BMI as the predictor variable, and the standard errors of the estimate were about twice as high for BCM, FFM, and TBW.

DISCUSSION

The purpose of this study was to develop predictive models to predict BCM, FFM and TBW for use in nutritional studies of HIV-infected individuals. The requirements for the models included applicability in normally nourished and malnourished individuals and suitability for clinical investigations in field situations. To be suitable for field studies, the technique must have a minimum of interoperator variability, and it should be inexpensive, easy to use and portable. The use of BIA and the derived models described above satisfy these requirements.

Bioimpedance analysis is a relatively new technique for assessing body composition in clinical settings (1). BIA is noninvasive, takes only a few minutes, and requires no active collaboration of patients. The analyzer is portable, relatively inexpensive, and the raw data is reproducible to less than 1%. Bioimpedance theory is based upon the concept of the body as an ionic conductor whose resistance depends upon length and cross sectional area (volume), the ionic composition of the conducting volume, and the frequency of the driving current (4). However, the human body is not uniform in either length, cross-sectional area or ionic composition, which may affect the response to BIA and the accuracy of the results.

Bioimpedance has two components, resistance and reactance (capacitance). At high frequencies, total body water is the conducting medium while, at low frequencies, the lipid component of the membranes of the BCM act as capacitors, which limit the flow of intracellular ions. The standard frequency for BIA, 50 kH, is sufficiently high that it is able to estimate total body water, though a small and variable effect of membrane capacitance is observed (25). BIA has been used to determine total body water, with a precision of 2–8% compared to isotope dilution (7–16). The addition of the reactance measurement did not improve the predictability of TBW as shown in other studies. The use of reactance also added little to the prediction of fat free mass. On the other hand, addition of reactance to the predictive model in this study greatly increased the accuracy of estimating TBK.

Several techniques were used to maximize the accuracy of the predictive models. The improved accuracy of the parallel transformed value of Xc instead of the reported value (Table 3) is consistent with the view of the BIA circuit as a parallel circuit containing a resistor and a capacitor, with the BCM representing a capacitor (FIG. 1). In contrast, FFM and TBW, which include the extracellular space as well as the BCM, were better predicted by R or by Z, which reflects the resistive component. The assumption that the human body can be viewed as a cylinder also was tested and a more accurate exponential function than $Ht^2/R$, Xc or Z was found. In addition, the use of gender-specific equations further improved accuracy, suggesting that the different basic geometric shapes of men and women affect the BIA measurement. Finally, the addition of weight to the predictive model also improved accuracy, though the improvement was modest, especially for the prediction of BCM.

Both internal and external validation studies were performed. The predictive models appear to be equally accurate in whites, blacks, and hispanics, as well as in controls and in patients infected with HIV. It should be noted that race and gender both influence the normal ranges of body composition. However, these factors do not affect the ability of bioimpedance to estimate their size. For the same reason, the accuracy of predicting BCM, FFM and TBW in HIV-infected subjects and controls were very similar, though the absolute values in the HIV-infected subjects were lower.

Body cell mass, as represented by TBK, has been considered to reflect most closely the body's metabolic tissues. BCM was defined by Moore as the oxygen-requiring, carbon-dioxide producing, glucose-burning cellular mass (26). Estimation of its size is difficult as it is a complex compartment, comprised of all non-adipose cells, as well as the aqueous compartment of adipocytes. Several techniques have been employed, though all are subject to error. Total body potassium content has been considered an accurate reflection of BCM since more than 97% of all the potassium in the body is intracellular in location (18). TBK was used as the measurement of BCM in this study. The relationship between TBK and BCM is dependent upon an assumed constant potassium concentration in the intracellular space (27). However, altered intracellular potassium concentration has been documented in AIDS patients (19) as well as in other diseases. Intracellular water volume, calculated as the difference between TBW and extracellular water volumes as determined by probe dilutional analysis, is another measure of BCM, and is based upon the knowledge that the intracellular space normally is maintained at the expense of the extracellular space. However, as stated above, this relationship also may be altered as a result of malnutrition (19,28). Total body nitrogen, as a reflection of total body protein, also has been used to estimate BCM, since constant proportions of the body's nitrogen normally are distributed between intracellular and extracellular proteins, the latter including structural and transport proteins (29). However, the relationship between intracellular and extracellular structural proteins is altered as a result of wasting in AIDS and other diseases, since intracellular proteins are more rapidly depleted than are structural proteins such as collagen (30). In addition, measurements of TBK, intracellular water volume and total body nitrogen require expensive and complex machinery and are not available outside of specialized research centers. For this reason, measurements of BCM usually are not employed in nutritional investigations.

While body weight may be a relatively accurate reflection of nutritional status and body cell mass in normal individuals, it is subject to gross errors in disease states due to fluid overload associated with cardiac, renal or hepatic diseases as well as hypoalbuminemia, or dehydration from diarrhea or poor fluid intake, none of which affect nutritional status directly. Calculation of fat free mass from anthropometric measurements, densitometry or even BIA may be used to predict BCM, but also may be inaccurate. The usefulness of these techniques is limited by their inability to distinguish body cell mass (BCM) from extracellular water volume, two components of fat free mass. In particular, errors might occur in the prediction of BCM in malnourished or otherwise ill patients, due to an alteration in the distribution of water in the body, with an increase in the relative extracellular space at the expense of the intracellular space, as shown in several clinical situations, including people with AIDS (19,28).

The predictive models derived using BIA were compared to predictions made using weight or BMI. In the comparison shown (Table 8), the standard errors of the estimate for weight or BMI were about double the errors for the BIA model. These results suggest that measurements using weight or BMI would have the same statistical power for detecting significant differences as BIA if a group four times larger were studied. However, the use of weight or BMI as a predictor of BCM, FFM, or TBW assumes normal relationships between the body compartments, including BCM/weight and TBW/FFM. Recent studies from our laboratory and others have indicated that these relationships may not be constant, especially after nutritional therapies, which further confounds their use. Megestrol acetate was shown to promote food intake and significantly increase body weight in AIDS patients (31). However, analysis of BIA results indicated that BCM did not change significantly during therapy, while body fat content rose substantially. The administration of recombinant growth hormone to AIDS patients led to a mild increase in weight, which consisted of a large increase in FFM plus a marked decrease in body fat content (32). Analysis of hydration status in HIV-infected and control subjects revealed that AIDS patients with malabsorption syndromes were significantly dehydrated and had significantly decreased TBW/FFM compared to AIDS patients without malabsorption and to controls (33). The use of weight or BMI to predict BCM would lead to an overestimation of the gain after megace therapy, an underestimation of the gain after growth hormone therapy, and an overestimation of BCM depletion in patients with malabsorption. Such inaccuracies may be avoided by the use of BIA.

CONCLUSION

The results of these studies indicate that BCM, FFM and TBW can be estimated using simple, inexpensive, and easily applied techniques. The estimates are sufficiently precise for use in clinical investigation. Further validation of the technique in other clinical situations as well as demonstration of the ability to accurately detect changes in body composition (34–36) are needed to determine the full applicability of BIA for nutritional evaluation and monitoring of nutritional support.

References

1. Lukaski H. C. Methods for the assessment of human body composition: traditional and new. Am J Clin Nutr 1987;46:537–56.
2. Cohn S. H. New concepts of body composition. In Ellis K. J., Yasumura S, Morgan W. D., eds. In vivo body composition studies. Oxford: Bocardo Press Limited 1987:1–11.
3. Jeejeebhoy K. N., Detsky A. S., Baker J. P. Assessment of nutritional status. JPEN 1990;14(suppl 5):193S–6S.
4. Kushner R. F. Bioelectrical impedance analysis: A review of principles and applications. J Am Coll Nutr 1992;11:199–209.
5. Lukaski H. C., Bolonchuk W. W., Hall C. B., Siders W. A. Validation of tetrapolar bioelectrical impedance method to assess human body composition. J Appl Physiol 1986;60:1327–32.
6. Kushner R. F., Schoeller D. A. Estimation of total body water by bioelectrical impedance analysis. Am J Clin Nutr 1986;44:417–24.
7. Jackson A. S., Pollack M. L., Graves J, Mahar M. T. Reliability and validity of bioelectrical impedance in determining body composition. J Appl Physiol 1988;64:529–34.
8. McDougall D., Shizgall H. M. Body composition measurements from whole body resistance and reactance. Surg Forum 1986;37:42–4.
9. Lukaski H. C., Johnson P. E., Bolonchuk W. W., Lykken G. I. Assessment of fat-free mass using bioelectrical impedance measurements of the human body. Am J Clin Nutr 1985;41:810–7.
10. Young R. E., Sinha D. P. Bioelectrical-impedance analysis as a measure of body composition in a West Indian population. Am J Clin Nutr 1992;55:1045–50.
11. Conlisk E. A., Haas J. D., Martinez E. J., Flores R., Rivera J. D., Martorell R. Predicting body composition from anthropometry and bioimpedance in marginally undernourished adolescents and young adults. Am J Clin Nutr 11992;55:1051–9.
12. Schols AMWJ, Wouters EFM, Soeters P. B., Westerterp K. R. Body composition by bioelectrical-impedance analysis compared with deuterium oxide and skinfold anthropometry in patients with chronic obstructive pulmonary disease. Am J Clin Nutr 1991;53:421–4.
13. Segal K. R., Burastero S, Chun A, Coronel P, Pierson R. N. Jr., Wang J. Estimation of extracellular and total body water by multiple frequency bioelectrical impedance measurement. Am J Clin Nutr 1991;54:26–9.
14. Johnson H. L., Virk SPS, ayclin P, Barbieri T. Predicting total body water and extracellular fluid volumes from bioelectrical measurements of the human body. J Am Coll Nutr 1992;11:539–47.
15. Sluys TEMS, van der Ende M. E., Swart G. R., van den Berg JWO, Wilson J. H. P. Body composition in patients with acquired immunodeficiency syndrome: a validation study of bioelectrical impedance analysis. JPEN 1993;17:404–6.
16. Lohmann T. G. Research progress in validation of laboratory methods of assessing body composition. Med Sci Sports Exerc 1984;16:596–603.
17. Centers for Disease Control.Classification system for human T-lymphocytotropic virus type III-lymphadenopathy-associated virus infections. Ann Intern Med 1986;105:234–7.
18. Pierson R. N. Jr., Lin D. H. Y., Phillips R. A. Total-body potassium in health: effects of age, sex, height, and fat. Am J Physiol 1974;226:206–12.
19. Kotler D. P., Wang J, Pierson R. Studies of body composition in patients with the acquired immunodeficiency Syndrome. Am J Clin Nutr. 1985;42:1255–65.
20. Pierson R. N. Jr., Wang J, Thornton J. C., et al: Body potassium by four-pi$^{40}$ K counting: an anthropometric correction. Am J Physiol 1984;246:F234–239.
21. Heymsfield S. H., Wang J., Funfar J., Kehayias J. J., Pierson R. N. Dualk photon absorptiometry: accuracy of bone mineral and sft tissue mass measurements in vivo. Am J Clin Nutr 1989;49:1283–9.
22. Pierson R. N. Jr., Wang J., Colt E. W., Neumann P. Body composition measurements in normal man: The potassium, sodium, sulfate and tritium spaces in 58 adults. J Chron Dis 1982;35:419–428.
23. Pethig R. Dielectric and electronic properties of biological materials. 1979, John Wiley & Sons, New York
24. Geddes L. A., Baker L. E. Principles of applied biomedical instrumentation. 3rd Edition, 1989, John Wiley & Sons, New York 25. Baumgartner R., Chumlea C., Roche A. Bioelectrical impedance for body composition. In: Pandolf K., Holloszy J., eds. Exercise and sports sciences reviews. Vol 18. Baltimore, Williams and Wilkins, 1990:193–225.
26. Moore F. D., Boyden C. M. Body cell mass and limits of hydration: their relation to estimated skeletal weight. Ann NY acad Sci 1963;110:62–71.
27. Moore F. D., Olesen K. H., McMurray J. D., Parker H. V., Ball M. R, Boyden CM. *The Body Cell Mass and its Supporting Environment*. Philadelphia, W. B Saunders, 1963.
28. Barac-Nieto M., Spurr G. B., Lotero H., Maksud M. G. Body composition in chronic undernutrition. Am J Clin Nutr 1978;31:23–40.

29. James H. M., Dabek J. T., Chettle D. R., et al. Whole body cellular and collagen nitrogen in healthy and wasted man. Clin Sci 1984;67:73–82.
30. Kotler D. P., Tierney A. R., Dilmanian F. A., et al. Correlation between total body potassium and total body nitrogen in patients with acquired imunodeficiency syndrome. Submitted for publication.
31. Babameto G., Kotler D. P., Burastero S., Wang J., Pierson R. N. Alerations in hydration in HIV -infected individuals. (Abstract) Clin Res. 1994;42:279A.
32. Schembelan M., LaMarca A., Mulligan K., Grunfeld C., Kennedy S., Breitmeyer J., Daar E. Growth hormone threrapy of AIDS wasting (Abstract). Proc X International Conference on AIDS 1994;2:35.
33. Engelson E. S., Tierney A. R., Pi-Sunyer F. X., Kotler D. P. Effects of megestrol acetate therapy upon body composition and serum testosterone in patients with AIDS. (Abstract) Clin Res. 1994;42:281A.
34. Deurenberg P., Weststrate J. A., Hautvast JGAJ. Changes in fat-free mass during weight loss measured by bioelectrical impedance and densitometry. Am J Clin Nutr 1989;49:33–6.
35. Vazquez J. A., Janosky J. E. Validity of bioelectical-impedance analysis in measuring changes in lean body mass during weight reduction. Am J Clin Nutr 1991;54:970–5.
36. Forbes G. B., Simon W., Amatruda J. M. is bioimpedance a good predictor of body-composition change? Am J Clin Nutr 1992;56:4–6.

TABLE 1

STUDY GROUPS

|  | HIV+ | HIV– |
|---|---|---|
| WHITE MALES | 60 | 60 |
| WHITE FEMALES | 7 | 22 |
| BLACK MALES | 21 | 25 |
| BLACK FEMALES | 12 | 62 |
| HISPANIC MALES | 24 | 16 |
| HISPANIC FEMALES | 10 | 13 |

TABLE 2

BODY COMPOSITION RESULTS

|  | WM | BM | HM | WF | BF | HF |
|---|---|---|---|---|---|---|
| CONTROL GROUP | | | | | | |
| WEIGHT | 69.4 ± 6.6 | 71.7 ± 11.8 | 76.2 ± 7.6 | 61.0 ± 8.4 | 68.8 ± 9.9 | 62.1 ± 6.7 |
| HEIGHT | 175.6 ± 6.9 | 173.6 ± 5.8 | 174.0 ± 6.7 | 166.0 ± 5.4 | 164.2 ± 6.1 | 160.2 ± 5.5 |
| BMI | 22.4 ± 1.3 | 22.1 ± 1.9 | 24.7 ± 1.9 | 22.2 ± 3.1 | 25.5 ± 3.3 | 24.3 ± 3.1 |
| TBK | 3773 ± 432 | 3583 ± 510 | 3839 ± 475 | 2425 ± 343 | 2626 ± 441 | 2204 ± 243 |
| TBK/HT | 21.4 ± 2.2 | 20.6 ± 2.3 | 22.3 ± 2.1 | 14.6 ± 1.9 | 16.0 ± 2.2 | 13.7 ± 1.4 |
| FFM | 61.4 ± 5.3 | 60.0 ± 6.5 | 59.5 ± 6.6 | 43.4 ± 4.4 | 44.0 ± 5.2 | 39.9 ± 3.0 |
| FAT | 8.1 ± 3.8 | 11.7 ± 7.0 | 17.8 ± 4.6 | 17.9 ± 7.1 | 24.8 ± 8.8 | 22.2 ± 6.1 |
| HIV+ GROUP | | | | | | |
| WEIGHT | 63.8 ± 9.7 | 63.1 ± 9.4 | 58.9 ± 10.6 | 49.8 ± 6.3 | 49.5 ± 6.4 | 51.6 ± 14.0 |
| HEIGHT | 176.5 ± 6.0 | 176.4 ± 7.9 | 168.1 ± 7.9 | 161.8 ± 1.9 | 165.4 ± 5.9 | 160.9 ± 5.3 |
| BMI | 20.5 ± 3.0 | 20.0 ± 3.1 | 20.7 ± 3.6 | 19.0 ± 2.2 | 19.0 ± 3.9 | 21.0 ± 4.9 |
| TBK | 3152 ± 552 | 3038 ± 528 | 2906 ± 552 | 2004 ± 186 | 2278 ± 382 | 1972 ± 427 |
| TBK/HT | 17.9 ± 3.1 | 16.5 ± 2.4 | 16.8 ± 3.3 | 12.1 ± 1.2 | 12.6 ± 4.7 | 12.0 ± 4.9 |
| FFM | 56.6 ± 5.5 | 55.6 ± 7.0 | 52.9 ± 7.8 | 39.6 ± 5.4 | 42.1 ± 3.9 | 37.2 ± 5.0 |
| FAT | 7.2 ± 4.3 | 7.6 ± 5.1 | 8.6 ± 3.5 | 10.2 ± 2.3 | 8.2 ± 5.2 | 14.4 ± 10.7 |

Data as mean ± sd, WM = white males, BM = black males, HM = hispanic males, WF = white females, BF = black females, HF = hispanic females, Weight, FFM, and fat in kg, TBK in meq

TABLE 3

COMPARISON OF MEASURED AND PARALLEL TRANSFORMED BIA VALUES

|  | SERIES MODEL | | PARALLEL MODEL | |
|---|---|---|---|---|
|  | r | SEE | r | SEE |
| BODY CELL MASS | | | | |
| $Ht^2/R$ | 0.81 | 13.8% | 0.81 | 14.1% |
| $Ht^2/Xc$ | 0.28 | 22.8% | 0.85 | 12.7% |
| $Ht^2/Z$ | 0.81 | 13.9% | 0.81 | 13.9% |
| FAT FREE MASS | | | | |
| $Ht^2/R$ | 0.88 | 9.1% | 0.87 | 9.3% |
| $Ht^2/Xc$ | 0.41 | 17.3% | 0.80 | 11.3% |
| $Ht^2/Z$ | 0.87 | 9.2% | 0.87 | 9.2% |
| TOTAL BODY WATER | | | | |
| $Ht^2/R$ | 0.85 | 9.8% | 0.84 | 9.9% |
| $Ht^2/Xc$ | 0.40 | 17.1% | 0.78 | 11.5% |
| $Ht^2/Z$ | 0.85 | 9.9% | 0.85 | 9.9% |

Data from males and females combined

TABLE 4

LOGARITHMIC TRANSFORMATIONS OF HEIGHT, REACTANCE AND IMPEDANCE

|  | All subjects | Males | Females |
|---|---|---|---|
| Body cell mass | $Ht^{2.23}/Xc_p^{0.42}$ | $Ht^{2.34}/Xc_p^{0.48}$ | $Ht^{2.12}/Xc_p^{0.36}$ |
| Fat free mass | $Ht^{1.43}/Z_p^{0.55}$ | $Ht^{1.45}/Z_p^{0.55}$ | $Ht^{1.41}/Z_p^{0.54}$ |
| Total body water | $Ht^{1.52}/Z_p^{0.67}$ | $Ht^{1.57}/Z_p^{0.71}$ | $Ht^{1.46}/Z_p^{0.62}$ |

TABLE 5

PREDICTIVE EQUATIONS FOR BODY COMPOSITION PARAMETERS

FAT FREE MASS

| | |
|---|---|
| Males | FFM = $0.54[Ht^{1.76}/(11.28)Xc_p^{0.31}] + 0.37(Wt) + 1.55$ |
| Females | FFM = $0.89[Ht^{1.91}/(51.87)Xc_p^{0.24}] + 0.10(Wt) - 1.07$ |

BODY CELL MASS

| | |
|---|---|
| Males | BCM = $0.76[(59.06)Ht^{1.60}/Xc_p^{0.50}] + 18.52(Wt) - 386.66$ |
| Females | BCM = $0.96[(1.30)Ht^{2.07}/Xc_p^{0.36}] + 5.79(Wt) - 230.51$ |

TOTAL BODY WATER

| | |
|---|---|
| Males | TBW = $0.58[Ht^{1.62}/(1.35)Z_p^{0.70}] + 0.32(Wt) - 3.66$ |
| Females | TBW = $0.76[Ht^{1.99}/(18.91)Z_p^{0.58}] + 0.14(Wt) - 0.86$ |

FFM as kg, BCM as meq potassium, TBW as liters

TABLE 6

COMPARISON OF MODEL AND VALIDATION SUBGROUPS

| | MODEL GROUP | | VALIDATION GROUP | |
|---|---|---|---|---|
| | r | SEE | r | SEE |
| BODY CELL MASS | 0.89 | 10.4% | 0.86 | 12.4% |
| FAT FREE MASS | 0.90 | 8.2% | 0.86 | 7.8% |
| TOTAL BODY WATER | 0.90 | 8.7% | 0.89 | 8.1% |

Predictions from non-gender specific equations; the BIA model used was the male and female combined group from Table 5. None of the differences were statistically significant.

TABLE 7

EFFECT OF RACE AND DISEASE UPON THE BIA PREDICTION

| | BCM | | FFM | | TBW | |
|---|---|---|---|---|---|---|
| | r | SEE | r | SEE | r | SEE |
| WHITE | 0.89 | 10.3% | 0.96 | 4.7% | 0.90 | 7.7% |
| BLACK | 0.89 | 10.6% | 0.95 | 6.0% | 0.90 | 7.6% |
| HISPANIC | 0.95 | 9.0% | 0.97 | 5.2% | 0.92 | 8.3% |
| HIV+ | 0.89 | 10.2% | 0.90 | 4.8% | 0.92 | 7.8% |
| CONTROLS | 0.92 | 9.5% | 0.96 | 5.8% | 0.90 | 7.7% |

Gender-specific equations

TABLE 8

COMPARISON OF WEIGHT, BMI, AND BIA PREDICTIVE MODELS

| | WEIGHT | | BMI | | BIA | |
|---|---|---|---|---|---|---|
| | r | SEE | r | SEE | r | SEE |
| BODY CELL MASS | 0.59 | 19.2% | 0.21 | 23.2% | 0.88 | 11.45% |
| FAT FREE MASS | 0.61 | 15.0% | 0.14 | 18.7% | 0.91 | 7.97% |
| TOTAL BODY WATER | 0.67 | 13.9% | 0.25 | 17.9% | 0.89 | 8.39% |

Predictions from non-gender specific equations; the BIA model used was the male and female combined group from Table 5.

What is claimed is:

1. A method for predicting body cell mass, fat free mass, and total body water of a person, said method comprising the steps of:

measuring height and weight of said person;

providing at least one signal representative of the measured height and weight;

measuring impedance of said person, said impedance comprising a resistance value and a reactance value;

correcting said measured impedance to indicate a value for said reactance in parallel to said resistance;

providing at least one signal representative of the corrected impedance;

calibrating at least one of the signals according to the sex of said person: and predicting body cell mass, fat free mass, and total body water of said person using the signals.

2. The method of claim 1, wherein the impedance measuring step comprises the step of using a bioimpedance analyzer.

3. The method of claim 2, wherein the bioimpedance analyzer is a single frequency bioimpedance analyzer.

4. The method of claim 1, wherein the predicting step further comprises determining body cell mass (BCM), fat free mass (FFM), and total body water (TBW) of the person, according to:

FFM=$0.54[Ht^{1.76}/(11.28)Z_p^{0.31}]+0.37(Wt)+1.55$ (for males);

FFM=$0.89[Ht^{1.91}/(51.87)Z_p^{0.24}]+0.10(wt)-1.07$ (for females);

BCM=$0.76[(59.06)Ht^{1.60}/Z_p^{0.50}]+18.52(Wt)-386.66$ (for males);

BCM=$0.96[(1.30)Ht^{2.07}/Xc_p^{0.36}]+5.79(Wt)-230.51$ (for females);

TBW=$0.58[Ht^{1.62}/(1.35)Z_p^{0.70}]+0.32(Wt)-3.66$ (for males); and

TBW=$0.76[Ht^{1.99}/(18.91)Z_p^{0.58}]+0.14(Wt)-0.86$ (for females);

where:

Ht=height (cm)

$Xc_p$=parallel transformed reactance (ohms)

$Z_p$=parallel impedance (ohms)

Wt=weight (kg).

\* \* \* \* \*

UNITED STATES PATENT AND TRADEMARK OFFICE
CERTIFICATE OF CORRECTION

PATENT NO. : 5,615,689
DATED : April 1, 1997
INVENTOR(S) : Donald P. Kotler

It is certified that error appears in the above-indentified patent and that said Letters Patent is hereby corrected as shown below:

Col. 1, line 45, "$^2H_2O$" should read -- $^3H_2O$ -- ;

Col. 2, line 61, "that" should read -- than --;

Col. 3, line 37, "RESULTS" should appear on the following line, as a heading;

Col. 3, line 59, "$R_m$" should read -- $R_M$ --;

Col. 8, line 5, "11992" should read -- 1992 --;

Col. 8, line 53, "25. Baumgartner ..." should start a new line;

Col. 9, line 9, "Alerations" should read -- Alterations --;

Col. 9, line 27, "is" should reach --Is--; and

Col. 12, line 43, "$Z_p^{0.50}$" should read --$Xc_p^{0.50}$--.

Signed and Sealed this

Twenty-ninth Day of July, 1997

Attest:

BRUCE LEHMAN

*Attesting Officer*  *Commissioner of Patents and Trademarks*